United States Patent [19]

Seufert et al.

[11] Patent Number: 4,658,071
[45] Date of Patent: Apr. 14, 1987

[54] PREPARATION OF OLEFINICALLY UNSATURATED COMPOUNDS IN PARTICULAR ALKENOLS

[75] Inventors: Walter Seufert, Speyer; Norbert Goetz, Worms; Rainer Becker, Bad Durkheim, all of Fed. Rep. of Germany; Volker Schwendemann, Mountain Lakes, N.J.

[73] Assignee: BASF Aktiengesellschaft, Fed. Rep. of Germany

[21] Appl. No.: 802,202

[22] Filed: Nov. 25, 1985

[30] Foreign Application Priority Data

Dec. 4, 1984 [DE] Fed. Rep. of Germany ....... 3444112

[51] Int. Cl.$^4$ ..................... C07C 29/17; C07C 33/025
[52] U.S. Cl. .................................... 568/903; 549/356; 556/466; 560/255; 560/261; 568/626; 568/687
[58] Field of Search ....................... 568/903, 626, 687; 556/466; 549/356; 560/255, 261

[56] References Cited

U.S. PATENT DOCUMENTS

| | | | |
|---|---|---|---|
| 2,883,431 | 4/1959 | Chase et al. | 568/903 |
| 3,192,168 | 6/1965 | Grenet | 568/903 |
| 3,407,227 | 10/1968 | Beck et al. | 568/903 |
| 3,450,776 | 6/1969 | DiCio et al. | 568/903 |
| 3,715,404 | 2/1973 | Lindler et al. | 568/903 |
| 4,273,944 | 6/1981 | Ohno et al. | 568/903 |

FOREIGN PATENT DOCUMENTS

| | | | |
|---|---|---|---|
| 1115238 | 10/1961 | Fed. Rep. of Germany | 568/903 |
| 12326 | 2/1981 | Japan | 568/903 |
| 181091 | 9/1966 | U.S.S.R. | 568/903 |

OTHER PUBLICATIONS

Houben-Weyl, Methoden der Organischen Chemie, 4th edition, vol. 4/1c, pp. 76 et seq. and 110 et seq.

Primary Examiner—J. E. Evans
Attorney, Agent, or Firm—Keil & Weinkauf

[57] ABSTRACT

An olefinically unsaturated compound, in particular a very pure cis-isomer of an alkenylhydroxy compound of the formula $$CH_3(CH_2)_m-CH=CH-(CH_2)_n-OR \qquad (I),$$

where R is hydrogen or a protective group which can virtually be eliminated, m is from 1 to 12 and n is from 1 to 10, is obtained by catalytic partial hydrogenation of the corresponding acetylene derivative over a supported catalyst which contains from 0.05 to 5% by weight of palladium and from 0.05 to 15% by weight of zinc and/or cadmium.

5 Claims, No Drawings

PREPARATION OF OLEFINICALLY UNSATURATED COMPOUNDS IN PARTICULAR ALKENOLS

The present invention relates to a process for the preparation of olefinically unsaturated compounds by hydrogenating the corresponding acetylenically unsaturated compounds over a palladium catalyst. It relates in particular to the preparation of the cis-isomers of alkenyl compounds of the formula I

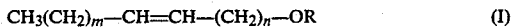

$$CH_3(CH_2)_m\text{—}CH\text{=}CH\text{—}(CH_2)_n\text{—}OR \qquad (I)$$

where R is hydrogen or a protective group which can be eliminated, eg. an ether or ester radical, m is from 1 to 12 and n is from 1 to 10, by partial hydrogenation of the corresponding alkynyl compounds over a prehydrogenated supported catalyst which contains palladium.

For many purposes, in particular biological ones, for example with regard to scents, growth regulators and drugs, the purity of the compounds used is important; where the structure plays a role with regard to purity, the steric purity of the compounds employed is also important. These substances must be capable of being prepared in readily obtainable apparatuses, for example in glass laboratory or pilot-scale apparatuses, ie. it must be possible to dispense with the use of high pressure.

It is known that the addition of hydrogen at the C≡C triple bond takes place with the formation of the cis-olefin (cf. Houben-Weyl, Methoden der Organischen Chemie, 4th edition, volume 4/1 c, page 76 et seq. and 110 et seq.). With regard to the steric purity of the hydrogenation products, the Lindlar catalyst (palladium catalyst on calcium carbonate carrier with added lead acetate) generally proves superior to other catalysts and is also effective under atmospheric pressure. However, the Lindlar catalyst too gives substantial amounts of the trans-isomer in addition to the desired cis-isomer; experience has shown that the cis/trans ratio is close to 10:1 or is even more unfavorable.

Although the method described in Euorpean Pat. No. 11,439 appears to resuit in high steric purity, the proposed hydrogenation requires a hydrogen pressure as high as 5 bar in the autoclave, ie. the use of expensive special apparatuses, and a catalyst having a high content of noble metal, ie. from 5 to 10% of palladium, is necessary.

It is an object of the present invention to provide an industrially useful process which permits acetylenically unsaturated compounds, in particular fairly long-chain alkynols or their derivatives, to be hydrogenated to the cis-alkenols as completely as possible and with the production of a small amount of by-products. Many of the acetylenically unsaturated compounds can be obtained readily and in good purity.

We have found that this object is achieved by the process according to the claims. It is surprising that a palladium catalyst moderated with zinc or cadmium is capable of hydrogenating triple bonds very selectively to olefinic double bonds virtually under atmospheric pressure, the hydrogenation coming to a stop when the olefinic state is reached, ie. there being no need to limit the amount of hydrogen.

The catalyst used according to the invention contains palladium and zinc and/or cadmium, preferably on a calcium carbonate carrier. Other suitable carriers are silica gel, alumina, aluminum silicate and aluminum spinels. The palladium content is from $5\times10^{-2}$ to 5, preferably from $10^{-1}$ to 3, % by weight, based on the catalyst including the carrier and calculated as metal, while the content of zinc or of cadmium is from $5\times10^{-2}$ to 15, preferably from $10^{-1}$ to 10, % by weight. The weight ratio of zinc and/or cadmium to palladium can vary, for example from 100:1 to 1:300. Advantageous catalysts are those which contain a relatively small amount of palladium (eg. 0.1 to 2%) and a somewhat higher amount of zinc or of cadmium. The preparation of suitable palladium/zinc/cadmium catalysts is described in, for example, European Pat. No. 50,229 and German Laid-Open Application DOS No. 3,039,085.

The catalyst is generally used in the form of extrudates (for hydrogenation in a fixed bed) or as a powder (where a suspension is employed).

Particularly suitable solvents are alcohols, in particular $C_1$–$C_4$-alcohols, and mixtures of these with water; pure water is also suitable, although the compounds involved are generally only slightly soluble therein.

The reaction takes place sufficiently rapidly at as low a temperature as above about $-10°$ C. but is preferably carried out at slightly below room temperature. The required minimum hydrogen pressure is, as a rule, from atmospheric pressure to about 5 bar, preferably not more than 2 bar. Although it is possible to employ a pressure of 5 bar or higher, eg. as high as 10 bar, this is generally uneconomical and requires special apparatus since the reaction takes place very rapidly in this case. Furthermore, the desired success may not be achieved under excessively high pressure. The selectivity of the catalyst can be further increased if a (tertiary or quasi-aromatic) amine is present during the reaction. Examples of suitable amines are morpholines, quinolines, lower alkylamines and pyridine. For example, 4-methylmorpholine, ie. tertiary amine which can readily be separated off again, has proven useful and is used in an amount which in general need not exceed 15% by weight, based on the starting material.

In formula I, R is preferably hydrogen. Examples of suitable protective groups which are easy to eliminate and can replace the hydrogen are tetrahydropyran-2-yl trialkylsilyl, acetyl, tert.-butyl and benzyl. Of course, compounds in which R is not a protective group but a constituent of the end product, eg. an ester of the hydroxy compound with a saturated or unsaturated fatty acid or an ether, preferably an alkyl ether, can also be converted to the cis-olefin structure.

EXAMPLE 1

6212 g (34.8 moles) of dodec-9-yn-1-ol and 316 g of N-methylmorpholine are dissolved in 46 l of methanol in a 100 l glass flask, and 62 g of a catalyst (0.7% Pd and 3.1% of Zn on a $CaCO_3$ carrier) are suspended in the solution. Thereafter, the stirred suspension is flushed with nitrogen, and hydrogenation is carried out at from 0° to 5° C. and under a hydrogen pressure of 0.1 bar above atmospheric pressure until the absorption of hydrogen is complete. The methanol and morpholine are stripped off to give 6,200 g of dodec-9-en-1-ol containing 96.6% of the cis compound and 2.1% of the trans compound.

The results shown in the Table below are obtained using the above method, appropriately adapted.

TABLE 1

| Example | Alkenol | Amount of cis compound (%) | Amount of trans compound (%) |
|---|---|---|---|
| 2 | tetradec-9-en-1-ol | 97.4 | 2.1 |
| 3 | tetradec-11-en-1-ol | 96.2 | 3.0 |
| 4 | hexadec-11-en-1-ol | 96.7 | 2.5 |
| 5 | hexadec-7-en-1-ol | 98.6 | 1.4 |
| 6 | tetradec-5-en-1-ol | 95.4 | 2.6 |
| 7 | tetradec-7-en-1-ol | 96.0 | 1.8 |

EXAMPLES 8 TO 15

40 g of dodec-9-yn-1-ol are hydrogenated in each case in the presence of 1.2 g of N-methylmorpholine in 170 ml of methanol, the type and amount of catalyst being varied. In these examples, it should be noted that, because of the particularly small amounts, the reaction is difficult to control. The Examples are therefore comparable only with one another but not with the Examples above (compare Example 1 with Example 8).

TABLE 2

| Example | Catalyst % by weight/ $CaCO_3$ carrier | Amount of catalyst (g) | Amount of cis compound (%) | Amount of trans compound (%) |
|---|---|---|---|---|
| 8 | 0.7 Pd, 3.2 Zn | 0.4 | 94.0 | 2.9 |
| 9 | 0.7 Pd, 1.0 Zn | 0.4 | 92.7 | 4.4 |
| 10 | 0.3 Pd, 3.2 Zn | 0.4 | 88.8 | 5.9 |
| 11 | 2.9 Pd, 3.2 Zn | 0.4 | 92.7 | 5.0 |
| 12 | 2.9 Pd, 3.2 Zn | 0.05 | 87.6 | 6.2 |
| 13 | 0.7 Pd, 6.3 Zn | 0.4 | 95.5 | 4.2 |
| 14 | 0.7 Pd, 3.1 Zn 3.1 Cd | 0.4 | 95.0 | 3.2 |
| 15 | 0.7 Pd, 5.4 Cd | 0.4 | 94.0 | 3.7 |

EXAMPLES 16 AND 17

The reaction is carried out as described in Example 1, in methanol containing water. A water content of 1% was found to give a cis/trans ratio of 95.6 to 3.1, while a water content of 5% gave a cis/trans ratio of 93.6 to 4.2.

We claim:

1. A process for the preparation of the cis-isomer of an alkenyl compound of the formula $$CH_3(CH_2)_m\text{—}CH\!=\!CH\text{—}(CH_2)_n\text{—}OR \qquad (I)$$

where R is hydrogen, an ether or ester radical, or a protective group which can virtually be eliminated, m is from 1 to 12 and n is from 1 to 10 which process comprises: hydrogenating the corresponding acetylenically unsaturated compound at a pressure of from atmospheric pressure to 2 bars and at a temperature slightly below room temperature in the presence of a tertiary amine over a palladium catalyst, wherein a calcium carbonate supported catalyst which contains from 0.1 to 2% by weight of palladium and from 0.05 to 15% by weight of zinc or cadmium is used.

2. A process as set forth in claim 1, wherein the catalyst contains 3% by weight of palladium or less.

3. A process as set forth in claim 1 for the preparation of the cis-isomer of an alkenylhydroxy compound of the formula $$CH_3(CH_2)_m\text{—}CH\!=\!CH\text{—}(CH_2)_nOH \qquad (II).$$

4. A process as set forth in claim 3 for the preparation of Z-9-dodecenol, Z-9-tetradecenol, Z-11-tetradecenol or Z-11-hexadecenol.

5. A process as set forth in claim 1, wherein an N-alkylmorpholine is used as the tertiary amine.

* * * * *